United States Patent
Kuhn et al.

(10) Patent No.: US 8,489,168 B2
(45) Date of Patent: Jul. 16, 2013

(54) COEFFICENT DETERMINATION FOR BLOOD OXYGEN SATURATION AND TOTAL HEMOGLOBIN CONCENTRATION INDICES

(75) Inventors: Jonathan L. Kuhn, Ham Lake, MN (US); Can Cinbis, Shoreview, MN (US); David A. Anderson, Stanchfield, MN (US); James K. Carney, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 446 days.

(21) Appl. No.: 12/948,884

(22) Filed: Nov. 18, 2010

(65) Prior Publication Data
US 2012/0130208 A1 May 24, 2012

(51) Int. Cl.
*A61B 5/1455* (2006.01)
(52) U.S. Cl.
USPC .......................................... 600/331; 600/310
(58) Field of Classification Search
USPC ................. 600/310, 322, 323, 331, 332, 473, 600/476
See application file for complete search history.

(56) References Cited

U.S. PATENT DOCUMENTS

| | | | |
|---|---|---|---|
| 4,230,122 A | | 10/1980 | Lubbers |
| 5,879,294 A | | 3/1999 | Anderson |
| 5,902,326 A | | 5/1999 | Lessar |
| 6,049,727 A | * | 4/2000 | Crothall ........................ 600/310 |
| 6,377,840 B1 | | 4/2002 | Gritsenko |
| 6,473,632 B1 | | 10/2002 | Myers |
| 6,599,250 B2 | | 7/2003 | Webb |
| 6,615,064 B1 | | 9/2003 | Aldrich |
| 6,667,803 B1 | | 12/2003 | Flessland |
| 6,711,424 B1 | * | 3/2004 | Fine et al. ..................... 600/322 |
| 6,711,425 B1 | * | 3/2004 | Reuss ........................... 600/331 |
| 7,239,385 B2 | | 7/2007 | Schrmitz |

(Continued)

FOREIGN PATENT DOCUMENTS

WO 2010144668 A1 12/2010

OTHER PUBLICATIONS

Dean E. Myers, Noninvasive method for measuring local hemoglobin oxygen saturation in tissue using wide gap second derivative near-infrared spectroscopy, Journal of Biomedical Optics 10(3), 034017 (May/Jun. 2005).

(Continued)

*Primary Examiner* — Eric Winakur
(74) *Attorney, Agent, or Firm* — Evans M. Mburu; Stephen W. Bauer; Michael C. Soldner

(57) ABSTRACT

A first concentration of a chromophore corresponding to a measurement volume of an optical sensor is determined. A second concentration of the chromophore is obtained in the vicinity of the measurement volume corresponding to a change in at least one of a total concentration of the chromophore and a relative concentration of a first form of the chromophore to the total concentration of the chromophore in the measurement volume. Light remittance measurements including a first light wavelength and a second light wavelength are obtained corresponding to the first chromophore concentration and the second chromophore concentration. A coefficient for computing an index of a change in the chromophore concentration is computed using the difference between the first and second chromophore concentrations and the first and second light remittance measurements.

23 Claims, 6 Drawing Sheets

U.S. PATENT DOCUMENTS

| | | |
|---|---|---|
| 7,302,294 B2 | 11/2007 | Kamath |
| 7,512,431 B2 * | 3/2009 | Roberts .......................... 600/332 |
| 2003/0212316 A1 | 11/2003 | Leiden |
| 2004/0116814 A1 | 6/2004 | Stranc |
| 2007/0239052 A1 | 10/2007 | Bhunia |
| 2007/0239053 A1 | 10/2007 | Bhunia |
| 2007/0239215 A1 | 10/2007 | Bhunia |
| 2007/0255148 A1 | 11/2007 | Bhunia |
| 2008/0004513 A1 | 1/2008 | Walker |
| 2008/0208269 A1 | 8/2008 | Cinbis |
| 2008/0306390 A1 | 12/2008 | Cinbis |

OTHER PUBLICATIONS

David A. Benaron, Quantitative Clinical Non-Pulsatile and Localized Visible Light Oximeter: Design of the T-Stat (Trade Marked) Tissue Oximeter, Stanford University School of Medicine, Palo Alto, CA USA 94305.

(PCT/US2011/059875) PCT Notification of Transmittal of the International Search Report and the Written Opinion of the International Searching Authority.

* cited by examiner

COEFFICENT DETERMINATION FOR BLOOD OXYGEN SATURATION AND TOTAL HEMOGLOBIN CONCENTRATION INDICES

TECHNICAL FIELD

The disclosure relates generally to medical devices and, in particular, to a medical device for ambulatory monitoring of blood oxygen saturation and total hemoglobin concentration in the measurement volume of an optical sensor.

BACKGROUND

An uncalibrated index of oxygen saturation in blood can be determined using an implantable optical sensor measuring the attenuation of two light wavelengths, typically red and infrared. This oxygen saturation index (O2 index) is useful for monitoring short-term, relative changes in oxygen saturation to detect a physiological event or condition causing a relatively sudden or abrupt change in oxygen saturation. For example, the O2 Index can be used in detecting conditions or events affecting the oxygenation or hemodynamic status of a patient when changes occur over a relatively short period of time, e.g. within about 10 seconds, such as during an unstable cardiac arrhythmia.

The O2 is computed as a function of the normalized change in the attenuation of red light with respect to a baseline red light attenuation measurement and the normalized change in the attenuation of infrared light with respect to a baseline infrared light attenuation measurement. Depending on the selected value of coefficients applied to the red and infrared light terms used to compute the O2, the index can be influenced by both blood oxygen saturation and total hemoglobin concentration present in a measurement volume of the optical sensor. Other influences can sometimes cause the O2 to respond to oxygen saturation and hemoglobin concentration changes in unpredictable ways over relatively longer periods of time, limiting the usefulness of the O2 in longer-term monitoring applications.

A calibrated absolute oxygen saturation (StO2) can be obtained using a four wavelength optical sensor. Emission and measurement of four wavelengths however requires higher power and processing burden than a two wavelength measurement. A need remains for a device and method capable of efficient and reliable monitoring of oxygen saturation and hemoglobin concentration useful for both acute and chronic patient monitoring, including ambulatory patient monitoring.

DETAILED DESCRIPTION

Figure 1:
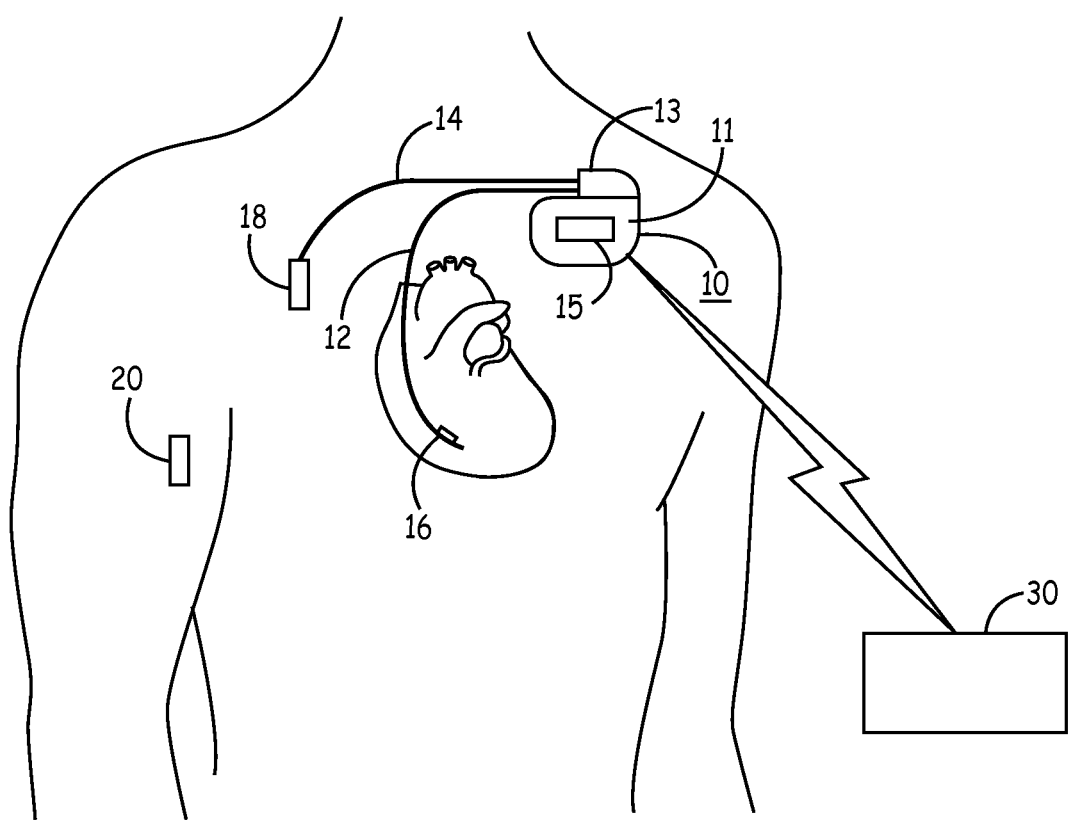
FIG. 1 is a schematic drawing of one example of an implantable medical device (IMD) configured for monitoring an O2 and a hemoglobin concentration (HC) index in a patient.

In the following description, references are made to illustrative embodiments. It is understood that other embodiments may be utilized without departing from the scope of the disclosure. In some instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic drawing of one example of an implantable medical device (IMD) 10 configured for monitoring an O2 and a hemoglobin concentration (HC) index in a patient. IMD 10 may be provided as a cardiac monitor, a pacemaker, an implantable cardiovertor defibrillator (ICD), or other device. IMD 10 may optionally be provided with therapy delivery functions, e.g. cardiac pacing, cardioversion or defibrillation.

IMD 10 may alternatively be embodied as a device used for monitoring other patient conditions, including, for example, diabetes, respiratory conditions, or neurological conditions. IMD 10 may be configured as a monitoring only device to record physiological data, detect events, and report data to an external device for analysis and review by a clinician. IMD 10 may alternatively be configured to detect events and respond to a detected event or condition by automatically delivering a therapy. A therapy may be an electrical stimulation therapy or a pharmaceutical or biological fluid therapy.

IMD 10 includes a housing 11 enclosing circuitry and components of IMD 10 and a connector block assembly 13 for connecting leads 12 and 14 extending from IMD 10 to the circuitry and components enclosed in housing 11. IMD 10 is shown coupled to a transvenous lead 12 carrying an optical sensor 16 and an extravascular lead 14 carrying an optical sensor 18. The lead locations and configurations shown are intended to illustrate various possible configurations and implant locations of an optical sensor used for monitoring an O2 and a HC index.

The transvenous lead 12 may carry an optical sensor 16 for measuring an O2 in venous blood, either within a vein or within a right heart chamber as shown. The extravascular lead 14 may be tunneled subcutaneously, submuscularly or within the thoracic or abdominal cavity for placing sensor 18 against a tissue targeted for monitoring an O2 and a HC index. Sensor 18 may be used to measure an O2 and HC index in an adjacent, blood perfused tissue.

In some embodiments, a leadless optical sensor 20 may be implanted at a desired body location and configured for wireless telemetric communication with IMD 10 or directly to an external device 30, which may be embodied as a medical device programmer, home monitor, computer, or other external or bedside monitoring or therapy delivery device. An optical sensor 15 may additionally or alternatively be incorporated on housing 11 or within IMD 10 and exposed through optical windows formed in the housing 11.

Numerous configurations of an optical sensor positioned for obtaining light attenuation measurements for use in monitoring an O2 and/or a HC index are possible and not limited to the configurations shown in FIG. 1. A sensor may be positioned extravascularly, adjacent a blood perfused tissue, or intravascularly.

Figure 2:
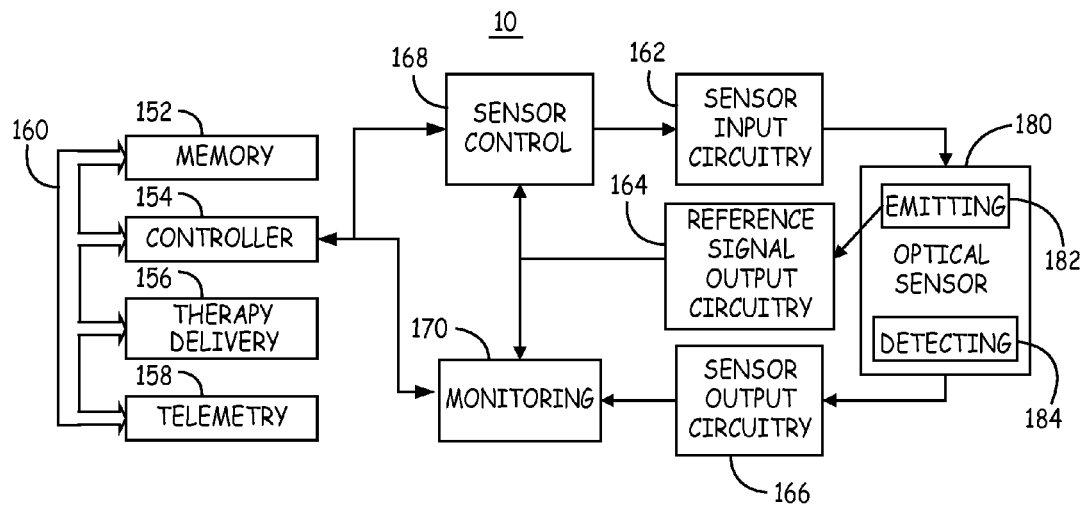
FIG. 2 is a functional block diagram of IMD according to one embodiment.

FIG. 2 is a functional block diagram of IMD 10 according to one embodiment. IMD 10 includes (or is coupled to) an optical sensor 180, which may be incorporated in or on a housing of IMD 10 or carried by a lead extending from IMD 10 as shown in FIG. 1. IMD 10 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light emitting portion 182 and a light detecting portion 184. Light emitting portion 182 includes a light source for emitting light through blood or a blood perfused tissue of the patient. Light detecting portion 184 includes a light detector, also referred to herein as a "photodetector", for generating a signal representative of an intensity of remitted light.

Sensor input circuitry 162 is coupled to light emitting portion 182 to deliver drive signals applied to the light source(s) included in light emitting portion 182 to cause controlled light emission, e.g. controlled intensity, time duration and frequency. Light emitting portion 182 includes one or more light sources for emitting light that includes at least four spaced apart light wavelengths. Emitting portion 182 may emit light at discrete, spaced-apart wavelengths or a single white light source may be used.

Sensor input circuitry 162 is controlled by sensor control module 168 which coordinates the beginning time, duration, and frequency of drive signals produced by sensor input circuitry 162. Drive signals may be applied to cause sequential light emission at different wavelengths or simultaneous, frequency multiplexed light emission. It is recognized that reference to an "individual" or "one" wavelength can include a narrow bandwidth of wavelengths approximately centered on, or at least including, the specified individual wavelength emitted by a light source.

Sensor output circuitry 166 receives signals from light detecting portion 184 and demodulates and digitizes the signal to provide a digital signal to monitoring module 170. Sensor output circuitry 166 may include an analog-to-digital converter and flash memory for digitizing an analog output signal from detecting portion 184, providing the digitized signal to monitoring module 170, storing measurement results for future retrieval, as well as storing calibration coefficients.

During an index optimization procedure, monitoring module 170 uses the optical signal to compute a measurement of StO2 and a measurement of a total hemoglobin index (THI). StO2 is a calibrated measurement, expressed as a percentage, of the oxygen saturation of the hemoglobin present in the probe measurement volume. In other words, StO2 is the relative concentration of oxygenated hemoglobin as a percentage of the total hemoglobin (oxygenated plus deoxygenated). StO2 is largely independent of the total hemoglobin concentration in the probe measurement volume. THI is a unitless, calibrated measurement of the total hemoglobin concentration, i.e. both deoxygenated plus oxygenated forms of hemoglobin, present in the probe volume. THI is largely independent of the oxygen saturation of hemoglobin. StO2 and THI are computed using the attenuation measurements of multiple wavelengths measured by detecting portion 184.

The StO2 and THI measurements are in turn used by processor 154 to compute optimized coefficients defining an O2 and a HC index. The O2 index is an index of the change in oxygen saturation ($\Delta$StO2) that occurs over a period of time and HC index is an index of the change in THI ($\Delta$THI) over a period of time. It is recognized that changes in chromophore concentrations other than hemoglobin, e.g. myoglobin concentration changes, may contribute to measurements of the HC index. The term "HC index" is used herein because changes in other chromophore concentrations, such as myoglobin, are expected to be a relatively small contribution to the HC index over even relatively long time periods, such as weeks or months, over which the HC index may be monitored.

During normal monitoring, light emitting portion 182 is controlled to emit two light wavelengths, e.g. red and infrared, and light measured by detecting portion 184 is used to compute the O2 and HC index using the optimized coefficients stored by sensor output circuitry 166 or monitoring module 170.

In some embodiments, IMD 10 is coupled to electrodes for use in sensing intracardiac EGM signals or subcutaneous ECG signals for detecting and discriminating heart rhythms. IMD 10 may include other sensors for sensing physiological signals such as blood pressure, patient activity, patient posture, temperature, or the like. Such sensor signals may be used in combination with the monitored O2 and HC index for determining when a therapy is needed and delivered by therapy delivery module 156. Therapy delivery module 156 may include electrical pulse generation capabilities for delivering cardiac pacing pulses and cardioversion/defibrillation shocks or neurostimulation pulses. Therapy delivery module 156 may additionally or alternatively include a fluid delivery pump for delivering a pharmaceutical or biological fluid to the patient.

Data acquired by processor 154 relating to an O2, HC index, StO2 and THI may be stored in memory 152 and/or transferred to an external device 30 (FIG. 1) via wireless telemetry module 158 for review by a clinician. Processor 154 transmits data to and from memory 152, therapy delivery module 156, and telemetry module 158 via data/address bus 160.

Some embodiments include a reference photodetector in the light emitting portion 182 of sensor 180. Reference signal output circuitry 164 may then be included for receiving a light detection signal from the reference photodetector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of StO2 and THI measurements computed using stored calibration constants and assuming stable light emission intensity. Accordingly sensor control 168 may include comparators and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. Alternatively, monitoring module 170 uses changes in the emitted light intensity to adjust a computed StO2 and THI value.

Figure 3:
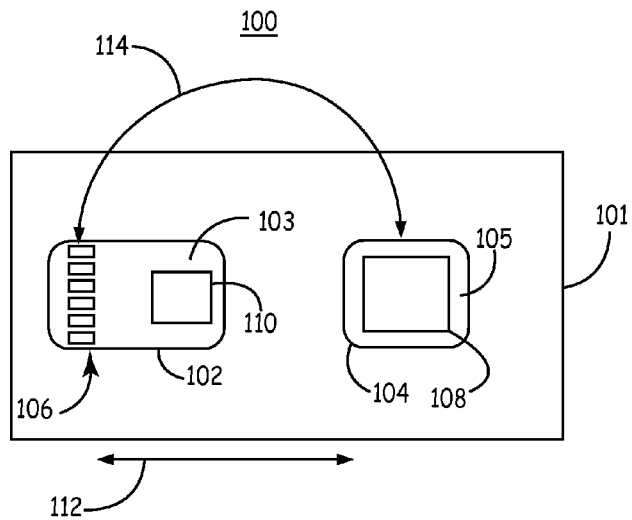
FIG. 3 is a top, schematic view of an optical sensor according to one embodiment.

FIG. 3 is a top, schematic view of an optical sensor according to one embodiment. It is recognized that numerous sensor configurations may be used and the methods for monitoring an O2 and HC index as described herein are not limited to any particular sensor configuration. In general, any optical sensor that acquires light attenuation measurements to enable computation of absolute StO2 may be used. Examples of other optical sensors that may be employed are generally described in commonly-assigned U.S. patent application Ser. No. 12/771,322 (Kuhn, et al.), hereby incorporated herein by reference in its entirety.

The sensor 100 shown in FIG. 3 includes a light emitting portion 102 and a light detecting portion 104. Light emitting portion 102 includes one or more light sources 106 positioned to emit light through a lens 103 sealed in an opening in hermetically-sealed housing 101. Light sources 106 are embodied as multiple light sources emitting light at separate spaced-apart wavelengths. In one embodiment, light sources 106 are embodied as light emitting diodes (LEDs) emitting light across the red and infrared light spectrum.

In one embodiment, six LEDs are provided emitting light in the red to infrared spectrum. Two LEDs emit red and infrared light, at 660 nm and 880 nm respectively, for use in measuring the O2 Index and HC index. Four more LEDs are provided to emit light at spaced apart wavelengths for computing second derivatives of the light attenuation spectra for use in computing calibrated absolute StO2 and THI measurements. The four wavelengths used for StO2 and THI measurements may be at 680 nm, 720 nm, 760 nm, and 800 nm. Alternatively, four wavelengths are measured including 660 nm, 720 nm, 760 nm and 800 nm where 660 nm and 800 nm are used for measuring the O2 and the HC index and all four are used for measuring StO2 and THI.

In other embodiments, one or more light sources are used to emit light that is measured at four or more light wavelengths including, for example, any in the range between approximately 660 nm and 890 nm such that remitted light corresponding to red and infrared wavelengths for computing an O2 Index and HC index and remitted light at four spaced apart wavelengths enabling a second derivative method for computing calibrated measures of StO2 and THI may be used. The calibrated measures of StO2 and THI are used to optimize the O2 Index and HC index as will be described in detail below. Any combination of LEDs (or other types of light sources) emitting light at any of the wavelengths mentioned herein may be used.

In the embodiment shown, the light emitting portion 102 further includes a reference light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the sensor materials encountered by emitted light before it reaches an adjacent tissue volume. Reference light detector 110 provides an output signal for measuring or detecting changes in the intensity of the light emitted by emitting portion 102.

The reference light detector 110 output signal can be used in computing or adjusting StO2 and THI measurements as described above in conjunction with FIG. 2. Additionally or alternatively, an output signal from reference light detector 110 can be used as a feedback signal for controlling the drive signals applied to light sources 106 to cause light emission.

In other embodiments, a light detector is not included in the emitting portion. The emitted light intensity is assumed to be stable throughout the usable life of the sensor so as not to introduce significant error in attenuation measurements.

The light detecting portion 104 includes a light detector 108 positioned to receive light through a lens 105 mounted in an opening in housing 101. The light detector 108 may be embodied as a photodiode and receives light scattered by an adjacent tissue volume. The distance 112 between the light sources 106 and the light detector 108 will influence the optical path length 114, shown schematically. Greater emitting-to-detecting separation distance (longer distance 112) will result in a longer optical path 114 extending deeper into the adjacent tissue volume than relatively shorter emitting-to-detecting separation distances.

Figure 4:
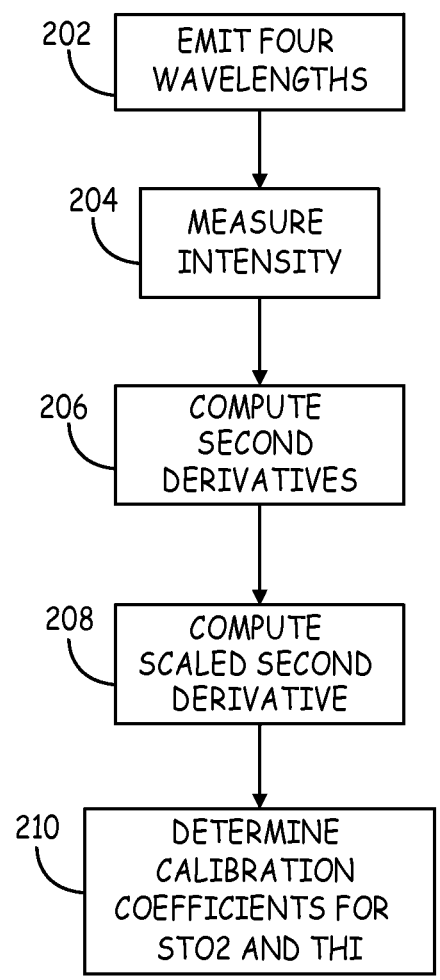
FIG. 4 is a flow chart of one method for determining a baseline oxygen saturation (StO2) and baseline total hemoglobin index (THI) for determining optimal coefficients used in computing an O2 and HC index.

FIG. 4 is a flow chart of one method for determining baseline StO2 and THI for use in determining optimal coefficients for computing an O2 and HC index. Flow chart 200 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Second derivative measurements of light attenuation are used to determine a concentration of a chromophore in a measurement volume of the optical sensor. In particular, a measurement of the concentration of total hemoglobin, i.e. the total hemoglobin index (THI), or a relative concentration of oxygenated hemoglobin to the total concentration of hemoglobin (deoxygenated plus oxygenated), i.e. the oxygen saturation (StO2), are determined. These measurements are calibrated and generally require light remittance measurements corresponding to at least four light wavelengths using the scaled second derivative method described herein.

The calibrated measurements of StO2 and THI are used to determine an optimal value of a coefficient used to compute an index sensitive to changes in the total concentration of the chromophore or a relative concentration of a first form of the chromphore to a second form of the chormophore. For example, the calibrated THI measurement is used to solve for an optimized coefficient used in computing a HC index that is sensitive to changes in the total concentration of hemoglobin, i.e., both oxygenated and deoxygenated hemoglobin. The calibrated StO2 measurement is used to solve for an optimized coefficient used in computing the O2 that is sensitive to the relative concentration of oxygenated hemoglobin to total hemoglobin concentration, i.e. oxygen saturation.

At block 202, the optical sensor is controlled to emit light at four wavelengths (or more). The intensity of the remitted light for at least four wavelengths is measured at block 204 to allow second derivatives, $D''(\lambda)$, of the light spectrum to be computed at block 206. In one embodiment, the remitted light is measured at wavelengths of 680 nm, 720 nm, 760 nm, and 800 nm. The second derivatives of the attenuation spectra are computed at the intermediate wavelengths, 720 nm and 760 nm, at block 206.

The second derivative at 720 nm is scaled by the second derivative at 760 nm, which can be expressed as $$SD''(720)=D''(720)/D''(760) \quad (1)$$

This scaled second derivative, SD''(720), is dependent on oxygen saturation and is independent of the total hemoglobin concentration present in the measurement volume and the optical path length. An absolute oxygen saturation, expressed as a percentage, can be defined as a function of the SD''(720) as follows:

$$StO2=Ae^{B(SD''(720))}+C \times SD''(720)+D \quad (2)$$

The coefficients A, B, C and D are determined through best-fit analysis of measurements of the scaled second derivative for calibration samples having known oxygen saturation at block 210.

The second derivative at 760 nm, D''(760), is dependent on the total hemoglobin present in the measurement volume, including oxygenated and deoxygenated hemoglobin. Light attenuation at 760 nm will be dependent on both total hemoglobin concentration and oxygen saturation. An oxygen saturation-insensitive THI can be defined as a function of the second derivative D''(760) when the D''(760) is corrected using an oxygen saturation-dependent slope term which compensates for the influence of oxygenated hemoglobin. An equation for THI can be given by:

$$THI=(M(SD''(720)) \times D''(760))/SF \quad (3)$$

The slope term, M(SD''(720)) is dependent on oxygen saturation and is determined as a calibration coefficient using samples of known oxygen saturation and hemoglobin concentration. When the slope term is selected correctly, THI is dependent on the total hemoglobin concentration and substantially insensitive to oxygen saturation. SF is a spacing factor that is used if the light emitting and light detecting portions are spaced apart at a different distance during calibration than after implantation. This term can be determined at calibration and may be omitted or set equal to one if the same sensor (or same separation distance) is used at calibration and in the implanted sensor.

Once calibrated, StO2 can be computed using Equation 2 when light remittance is measured at four wavelengths to allow computation of the second derivatives of the light attenuation spectra. A calibrated THI can be computed using Equation 3. The calibration coefficients in Equations 2 and 3 can be stored in the memory of the IMD and are used to compute StO2 and THI as needed. In particular, whenever the coefficients used to compute an O2 and a HC index from a two-wavelength light measurement need to be optimized, StO2 and THI are computed using the stored calibration coefficients and a four wavelength light measurement for use in the index optimization process as will be described further below.

Figure 5:
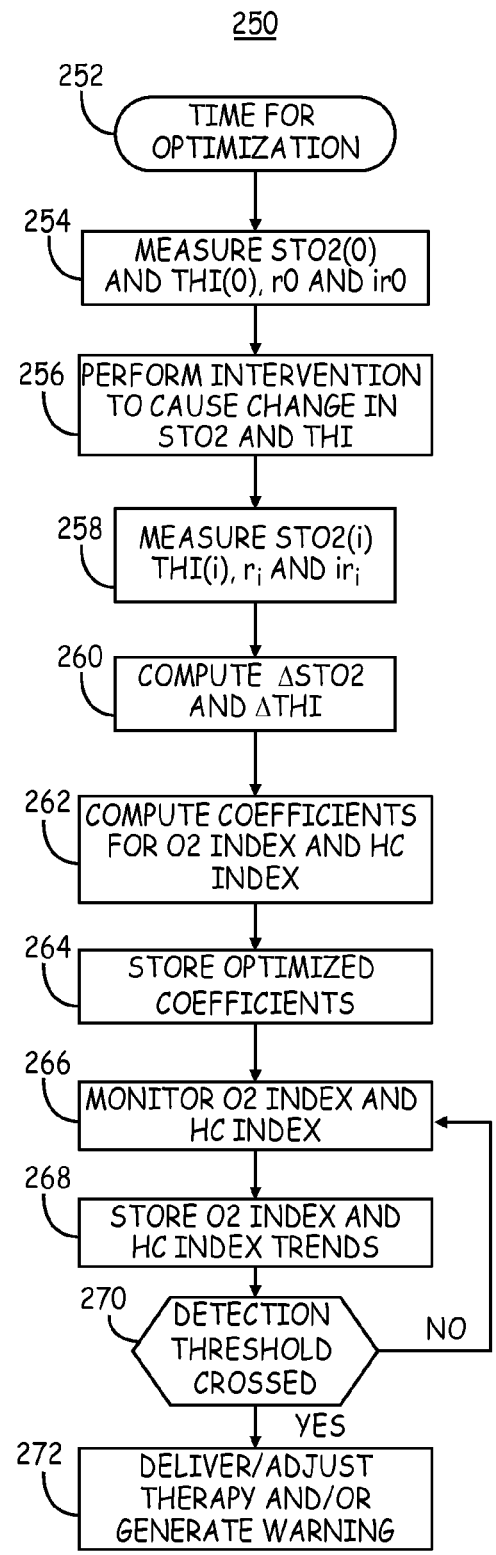
FIG. 5 is a flow chart of a method for optimizing an O2 and a HC index.

FIG. 5 is a flow chart 250 of a method for optimizing an O2 and a HC index. The process shown in flow chart 250 begins when the IMD determines that it is time to perform an optimization. An optimization is performed at implant to initially store optimal coefficients for computing an O2 and a HC index using two-wavelength light measurements. The optimization process may be repeated at regular time intervals or in response to receipt of a command from a programmer or other external device during an office visit or as part of a remote patient management routine. Depending on the duration of a monitoring protocol and use of the sensor, the coefficient optimization may need only performed once, at implant. When index coefficient values are established according to baseline StO2 and THI measurements only at implant, the measurement method used to obtain actual changes in absolute oxygen saturation and total hemoglobin concentration is not limited to the scaled second derivative method described here; other methods may be used for measuring oxygen saturation and hemoglobin concentration.

StO2 or THI may also be checked periodically to determine if a change in either one warrants a re-optimization of the O2 and HC index coefficients. The optimization process may also be performed in response to detecting a drift or change in the O2 or HC index or in response to detecting a change in another physiological signal, such as an accelerometer signal relating to patient physical activity, a cardiac electrogram or ECG signal, or heart sounds.

When the optimization process is started, initial baseline StO2(0) and THI(0) measurements are obtained at block 254. Corresponding baseline red ($r_0$) and infrared ($ir_0$) light are also measured at block 254. Baseline red ($r_0$) and infrared ($ir_0$) measurements are obtained for normalizing subsequent r and it light attenuation measurements used to compute the O2 and HC index as will be described below.

An intervention is then performed at block 256 intended to cause a change in oxygen saturation and/or hemoglobin concentration in the vicinity of the optical sensor. The intervention that is performed will depend on the implant location of the optical sensor, the type of device the process has been implemented in, and the setting in which the optimization is being performed. For example, if the sensor is implanted along a patient's arm, the patient may be instructed to perform an arm raise to cause a change in both oxygen saturation and hemoglobin concentration in the vicinity of the sensor. Such a maneuver may be safely performed by a patient independently at home or under limited or no clinical supervision.

If the process is being implemented in an ICD, the intervention performed at block 256 may be an automated VF induction that is routinely performed as part of the ICD implant procedure with trained clinical supervision and emergency treatment available. The VF induction process is performed automatically by the ICD upon receipt of a programmer command.

During an office visit, an inflatable cuff could be placed proximally around a limb when the sensor is implanted along a limb. Other interventions or maneuvers intentionally performed to obtain time-varying StO2 and THI measurements may include, but are not limited to, a breath hold or other prescribed breathing, Valsalva maneuver, Mueller maneuver, leg raise, postural change or positional change, use of a tilt table, application of heat or cold, pharmacological intervention, application of pressure, localized electrical stimulation, prescribed activity change, variation of breathing gasses (increase or decrease percentage of oxygen). These or other interventions or maneuvers may be customized for a particular patient, sensor implant location and monitoring application. The repeatability of the change in oxygen saturation and hemoglobin concentration in response to a particular intervention is not critical since any change in oxygen saturation and hemoglobin concentration which allows at least two different StO2 and THI measurements to be obtained is sufficient to optimize the O2 and HC index. As such, different interventions may be performed at different times and the response to a particular intervention need not be substantially the same each time it is performed, though similar trends would be expected.

After performing the intervention, at least one more StO2 and THI measurement is performed at block 258, with corresponding $r_i$ and $ir_i$ measurements. The change in StO2 (ΔStO2) and the change in THI (ΔTHI) are computed at block 260 relative to the baseline measurement. Using these calibrated changes in actual StO2 and THI and the two-wavelength r and it light measurements, the optimal coefficients for the O2 and the HC index can be computed at block 262.

The O2 may be expressed as:

$$O2\ Index = \Delta StO2 = a*R - b*IR \quad (4)$$

wherein R is the fractional change of the attenuation of red light ($r_i$) at approximately 660 nm normalized with respect to a baseline attenuation measurement ($r_0$), given by:

$$R = (r_i/r_0) - 1$$

and IR is the fractional change in the attenuation of infrared light ($ir_i$) at approximately 880 nm normalized with respect to a baseline attenuation measurement ($ir_0$), given by:

$$IR = (ir_i/ir_0) - 1.$$

Reference is made to U.S. Pat. No. 7,787,942 (Bhunia), hereby incorporated herein by reference in its entirety, as one example of the computation and use of an O2.

The baseline $r_0$ and $ir_0$ measurements may be measured at regular intervals, for example approximately every five or 10 seconds or another selected interval, with $r_i$ and $ir_i$ sampled at a desired sampling rate, e.g. every second, such that R and IR may be computed at the desired sampling rate using baseline $r_0$ and $ir_0$ measurements that are updated less frequently.

To optimize the coefficients "a" and "b" in Equation 4, a change in actual StO2 is measured under n different conditions (a minimum of two different conditions) and used to determine coefficients that yield an O2 Index having a high sensitivity to oxygen saturation change and low sensitivity (or insensitivity) to total hemoglobin concentration change.

Having measured StO2 under at least two different conditions to obtain n values of ΔStO2 with associated measurements of R(1) to R(n) and IR(1) to IR(n), a least mean squares fit or other similar techniques can be used to solve for the two unknowns, a and b, yielding a best fit equation with optimized coefficients for computing the O2 using Equation 4. The optimal coefficients may be solved for using oversampling of StO2 and regression methods to minimize the effect of signal noise in the measurement of StO2. For example, StO2, and $r_i$ and $ir_i$ measurements may be sampled once per second with baseline StO2(0), $r_0$ and $ir_0$ measurements is updated every 10 seconds or according to a predefined amount of change in StO2.

The sensitivity of the O2 to oxygen saturation and hemoglobin concentration will depend on the value of the coefficients chosen. The coefficients are dependent on the baseline StO2. A given coefficient value may be valid within a relatively narrow range of StO2, but outside that range the coefficients need to be re-optimized according to a new baseline StO2. In past practice, the "a" coefficient in Equation 4 used for computing an O2 has been nominally set as 1 and the b coefficient has been nominally selected as 1 or 1.5. A single constant universal value for the coefficients used in the O2 equation will result in an O2 that is sensitive to both oxygen saturation and hemoglobin concentration changes, when the true optimal coefficient values do not happen to coincide with the universal value chosen. Depending on the coefficients chosen, the O2 in some cases could be more dependent on hemoglobin concentration changes than on oxygen saturation changes. For a given baseline StO2 state there exists a numeric value of the coefficient that does isolate the blood oxygen saturation from total hemoglobin concentration, thereby yielding a pure index of oxygen saturation. However, this value depends on several factors, including baseline oxygen saturation and tissue scattering. As such, if significant change in baseline oxygen saturation occurs, the coefficients used to compute the O2 need to be updated to maintain a reliable O2 over selected monitoring intervals. The optimization of the O2 coefficient based on actual calibrated measurements of a baseline StO2 promotes high sensitivity to oxygen saturation changes and low sensitivity (or insensitivity) to hemoglobin concentration changes.

The HC index may be expressed by an equation having a similar form to the O2, differing in the numerical values of the coefficients only:

$$HC\ index = \Delta THI = c*R - d*IR \quad (5)$$

wherein R is the fractional change of the attenuation of red light ($r_i$) normalized with respect to a baseline attenuation measurement $r_0$, and IR is the fractional change in the attenuation of infrared light ($ir_i$) normalized with respect to a baseline attenuation measurement $ir_0$ (as given above).

To optimize the coefficients c and d in Equation 5, the change in THI measured under at least two different conditions is used to determine coefficients that yield a HC index having a high sensitivity to the change in hemoglobin concentration and low sensitivity (or insensitivity) to oxygen saturation changes.

Having measured ΔTHI under at least two different conditions to obtain n ΔTHI values with associated measurements of R(1) to R(n) and IR(1) to IR(n), a least mean squares fit or other curve fitting method can be used to solve for the two unknowns, c and d, at block 262, yielding a best fit equation with an optimized coefficient values for computing the HC index using Equation 5. Oversampling of THI, $r_i$ and $ir_i$ measurements and regression techniques may be used in solving for the optimal coefficient to overcome signal noise in the measurement of THI. The baseline THI(0), $r_0$ and $ir_0$ measurements may be acquired at regular intervals of time, e.g. approximately every 5 seconds or 10 seconds, or upon measuring a defined change in StO2 and/or THI. The measured $r_i$ and $ir_i$ may be sampled at a higher frequency with the terms $r_i/r_0$ and $ir_i/ir_0$ updated at the sampling frequency using the periodic baseline measurements $r_0$ and $ir_0$.

The optimized coefficients for O2 and HC index are stored at block 264. Each time an O2 or HC index measurement is needed according to a patient monitoring algorithm, the O2 and/or the HC index is monitored at block 266 by measuring the red and infrared light attenuation and computing the respective index using equation 4 or 5 and the stored, optimized coefficient. The monitoring of O2 and HC index performed at block 266 may occur on a periodic basis, such as once per minute, once per hour, daily, weekly, or another frequency or on a triggered basis in response to other physiological signals, a delivered therapy, or an external command.

The monitoring of O2 and/or HC index at block 266 using optimized coefficients is expected to provide reliable monitoring of relative changes in oxygen saturation and hemoglobin concentration. Without the optimization of the coefficients, only short term trends in the indices, for example less than one minute and typically less than 30 seconds or even smaller time intervals, may be reliable because of the dependence of the coefficients on the baseline oxygen saturation and THI and the resulting potential for sensitivity of the O2 to hemoglobin concentration changes and the potential for sensitivity of the HC index to oxygen saturation changes.

At block 268, data and trends relating to one or both indices may be stored. The indices may be compared to respective thresholds for detecting a physiological condition or event at block 270. A threshold applied to either of the O2 or HC index may be stored in a look-up table according to a measured baseline StO2 or measured baseline THI measurement, respectively. Alternatively, a threshold applied to either index may be defined as a function of the baseline StO2 and THI. If the patient has high baseline StO2 and THI, then the O2 undergo a greater change during a serious event or episode than in a patient that has a low baseline StO2 and THI prior to the event. A most recent StO2 or THI baseline may therefore be used to compute an updated threshold value applied to the respective O2 and HC index.

There may also be a dependence of index thresholds on the type of tissue being monitored, for example muscle tissue versus fat tissue. Index thresholds used to detect a clinical event or episode can be established clinically over a defined patient population.

If a clinical event or episode is detected, a therapy may be delivered or adjusted by the IMD at block 272, or the IMD may generate a patient or physician warning that is transmitted to an external device. Otherwise monitoring continues at block 266 until re-optimization of the index coefficients is needed.

Figure 6:
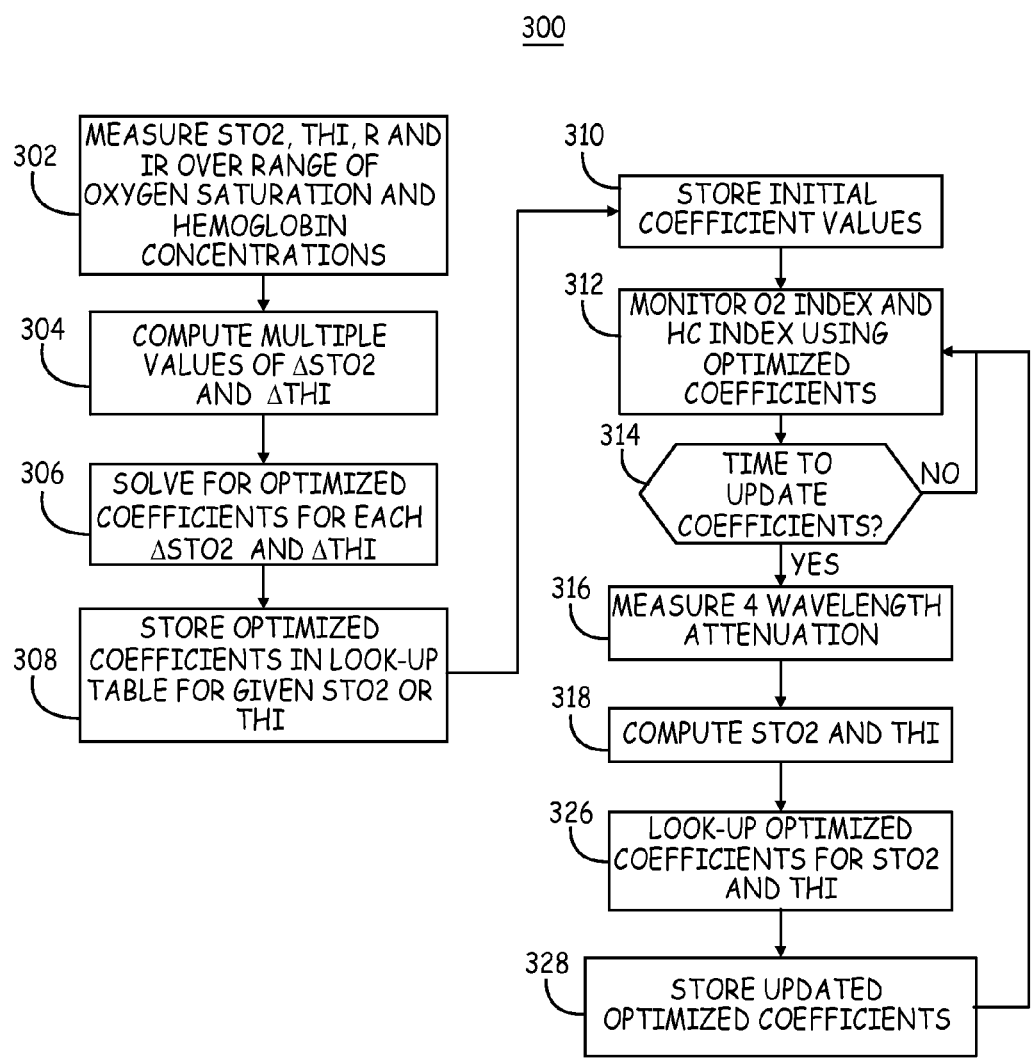
FIG. 6 is a flow chart of one method for implementing optimized O2 and HC index monitoring in an IMD.

FIG. 6 is a flow chart 300 of one method for implementing optimized O2 index and HC index monitoring in an IMD. In FIG. 5, n StO2 and THI measurements are used to solve for optimized coefficients for computing the O2 index and HC index as needed. In the alternative embodiment of FIG. 6, blocks 302 through 308 are performed a priori to establish a look-up table of optimized coefficient values according to baseline StO2 and THI values. At block 302, StO2, THI, R, and IR are measured over a range of both oxygen saturation and hemoglobin concentration. The ranges of StO2 and THI values may be established prior to implant using known samples, or at the time of implantation using an intervention intended to cause varying values of StO2 and THI, such as an arm raise, inflated cuff, VF induction or other maneuver. The ranges of StO2 and THI are intended to span an expected physiologic range of measurements that may be encountered during O2 and HC index monitoring.

During one or more maneuvers, StO2 and THI are measured using the second derivatives of light attenuation spectra across four spaced apart wavelengths. For each StO2 and THI measurement, r and it is also measured. For example, initial baseline measurements of StO2(0) and THI(0), $r_0$ and $ir_0$ may be made at time zero marking the onset of an arm raise or other maneuver. These "baseline" measurements are repeated at regular intervals thereafter, e.g. every five seconds or other desired interval, while the arm remains raised to obtain updated baseline StO2(0), THI(0), $r_0$ and $ir_0$ values over time for use in computing $\Delta$StO2, $\Delta$THI and R and IR. Baseline measurements may alternatively be updated based on a percentage change in StO2 or THI. The O2 and the HC index may be considered reliable within a range of StO2 and THI however if StO2 or THI varies outside that range, coefficients will need to be updated.

$StO2_i$, $THI_i$, $r_i$, and $ir_i$ are sampled at a desired sampling frequency, for example at 1 to 10 Hz, to obtain $\Delta$StO2, $\Delta$THI, R and IR measurements using the periodically updated baseline measurements, StO2(0), THI(0), $r_0$ and $ir_0$, and the sampled $StO2_i$, $THI_i$, $r_i$, and $ir_i$ measurements. From the multiple StO2 and THI measurements, n differences in StO2 and THI, i.e. n $\Delta$StO2 and n $\Delta$THI, can be computed at block 304. A best fit optimization is performed to compute the optimal coefficients for the respective Equations 4 and 5 at block 306 for the n $\Delta$StO2 and $\Delta$THI values and associated R and IR values.

At block 308, a look-up table of optimized coefficients is generated using the solutions computed at block 306. For each given value of StO2(0) (the baseline measurements), an optimized value for the coefficients a and b is stored. For each given baseline value of THI(0), an optimized value for the coefficients c and d is stored. Coefficient values may be interpolated from the optimization data to provide a uniform table of values. The look-up table is stored in the IMD memory such that the optimal coefficient values may be quickly extracted from the table to update optimal index coefficients upon measuring a baseline StO2 and THI without having to perform a computationally-intensive, best-fit equation optimization each time optimal coefficients are updated. The operations performed at blocks 302 through 308 need only be performed once to establish the look-up tables listing the coefficient values according to respective baseline StO2 and THI measurements.

Measurements of actual StO2 and total hemoglobin concentration performed to establish the coefficient look-up tables performed a priori are not limited to the scaled second derivative measurements described here. Other methods, including full spectroscopy methods, may be used to obtain actual StO2 and total hemoglobin concentration measurements for establishing the look up table of optimal coefficient values.

Monitoring the O2 and HC index with updating of the coefficients used to compute these indices as needed occurs at blocks 312 through 328. After storing the look-up table at block 308, initial coefficient values are stored at block 310. Initial coefficient values are determined by obtaining baseline StO2 and THI measurements and looking up the associated values for the coefficients a, b and c, d from the stored look-up tables.

In one embodiment, validation of the initial coefficient values may be performed at block 310 by repeating StO2 and THI baseline measurements prior to or at the onset of performing an intervention to cause a change in both oxygen saturation and hemoglobin concentration. A second StO2 and THI measurement is used to compute an actual $\Delta$StO2 and actual $\Delta$THI. The O2 and HC index are computed using the initial coefficient values. If the error between an estimated value of $\Delta$StO2 based on the O2 and actual measurement of $\Delta$StO2 and the error between an estimated value of $\Delta$THI based on the HC index and actual measurement of $\Delta$THI are both less than a threshold, e.g. 10%, the initial coefficient values are retained. Otherwise, the process of blocks 302 through 308 may be repeated to establish a new look-up table. At block 312, O2 index and/or HC index monitoring is performed according to a monitoring protocol using the initial coefficient values. If it is time to update the coefficients, as determined at block 314, e.g. on a periodic basis, a triggered basis, or based on increasing error between actual and estimated values of $\Delta$StO2 and/or $\Delta$THI, the four wavelengths needed to compute the SD"(720) and D"(760) are measured at block 316. From these measurements, new baseline StO2 and THI values are computed at block 318.

At block 326, the optimized coefficients for computing the O2 and the HC index are determined by looking up the respective coefficient values corresponding to the measured baseline StO2 and baseline THI values in the stored look-up table. The coefficient values found in the look-up table are stored as updated optimized coefficients, a, b and c, d, at block 328. O2 and HC index monitoring continues using the updated optimized coefficients at block 312.

In this way, four wavelength light measurements, which require additional power for light emission and computational burden to solve for StO2 and THI, are performed only when updates or coefficient optimization is needed to maintain an O2 sensitive to oxygen saturation changes and substantially insensitive to hemoglobin concentration changes and a HC index sensitive to hemoglobin concentration changes and substantially insensitive to oxygen saturation changes. In many clinical applications for monitoring a patient condition or detecting clinical events, relative changes in oxygen saturation or hemoglobin concentration are adequate for detecting a condition or event; calibrated absolute measurements are not necessary. In order to promote the reliability and accuracy of relative changes measured over relatively long periods of time, e.g. more than thirty seconds, the coefficient used to compute the O2 or HC index needs to be optimized to maintain the proper sensitivity to oxygen saturation or hemoglobin concentration, respectively, but not both. As such, the methods and apparatus described herein enable relative changes to be monitored over relatively long periods of time using optimized O2 and HC indices while minimizing the power and computational requirements that are needed as compared to monitoring calibrated absolute StO2 and THI measurements. The O2 and HC indices also benefit from having less electrical noise than StO2 and THI, because they are based on fewer signals.

Figure 7:
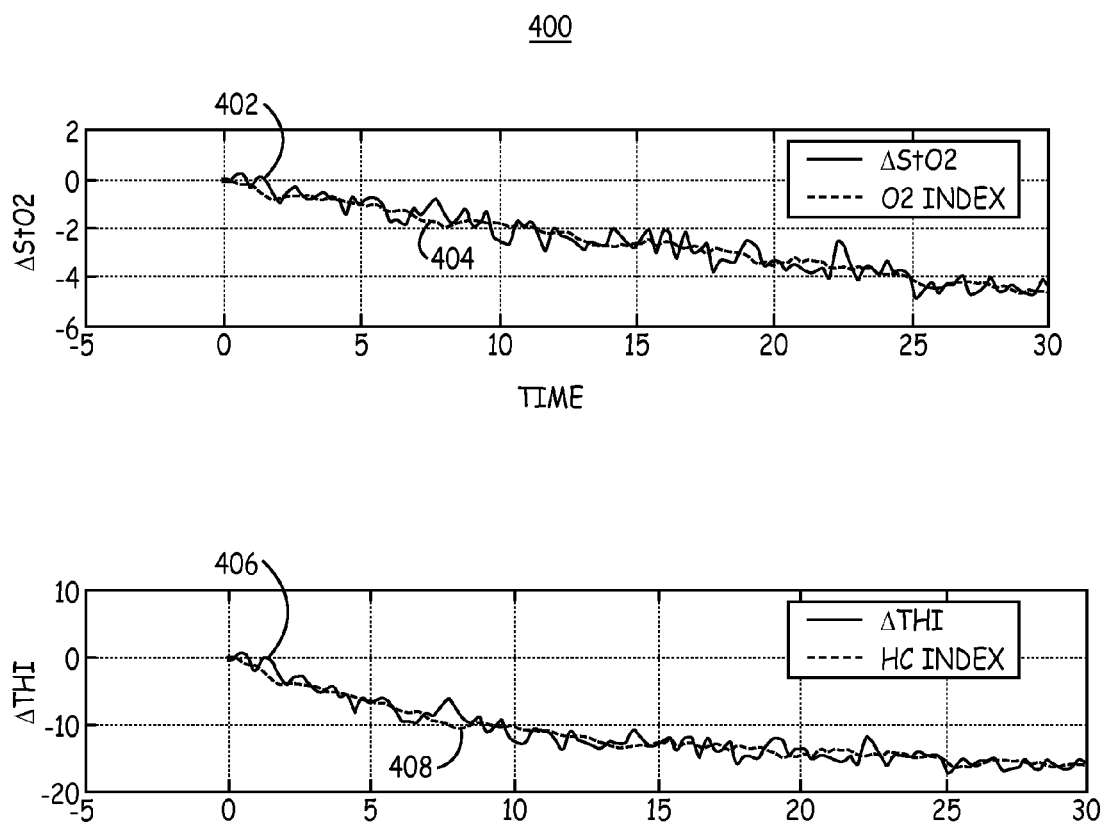
FIG. 7 is a time-based plot of actual and estimated change in StO2 and THI.

FIG. 7 is a time-based plot 400 of actual measured ΔStO2 402 and ΔTHI 406 after performing an intervention at time 0. In this example, ventricular fibrillation is induced at time 0 and both the measured ΔStO2 and ΔTHI exhibit an increasingly negative trend over time relative to the initial baseline (0) value. An estimated ΔStO2 404 computed as the optimized O2 using two-light wavelength measurements and Equation 4 above is shown to closely track the actual ΔStO2. Similarly, an estimated ΔTHI computed as the optimized HC index 408 using two-light wavelength measurements and Equation 5 above closely tracks the measured ΔTHI. As such, an O2 and an HC index computed using coefficients optimized according to baseline StO2 and THI measurements and requiring only two light wavelength measurements during normal monitoring provides an efficient and reliable method for monitoring relative changes in oxygen saturation and hemoglobin concentrations over short-term monitoring applications and enables long-term monitoring applications using two-wavelength light attenuation measurements with only periodic measurements of actual StO2 or THI.

Thus, a medical device and associated method for monitoring indices of oxygen saturation change and total hemoglobin concentration change have been presented in the foregoing description with reference to specific embodiments. It is appreciated that various modifications to the referenced embodiments may be made without departing from the scope of the disclosure as set forth in the following claims.

The invention claimed is:

1. A method for monitoring a patient condition using an implantable medical device including an optical sensor, the method comprising:
   obtaining a first concentration measurement of a chromophore in a vicinity of a measurement volume of the optical sensor, the chromophore present in a first form and a second form;
   performing an intervention to cause at least one of a change in a total concentration of the chromophore and a change in a relative concentration of the first form of the chromophore to the total concentration of the chromophore in the measurement volume;
   obtaining a second concentration measurement of the chromophore in the vicinity of the measurement volume after performing the intervention;
   obtaining a first measurement of light remittance comprising a first light wavelength and a second light wavelength, the first light remittance measurement corresponding to the first concentration;
   obtaining a second measurement of light remittance comprising the first light wavelength and the second light wavelength, the second light remittance measurement corresponding to the second concentration;
   solving for a coefficient for computing an index of a change in the chromophore concentration using a difference between the first and second chromophore concentration measurements and the first and second light remittance measurements;
   measuring remittance at the first light wavelength and the second light wavelength; and
   computing an index of the change in chromophore concentration using the measured remittance and the coefficient.

2. The method of claim 1, wherein the first and second chromophore concentrations correspond to a relative concentration of the first form of the chromophore to the total concentration of the chromophore.

3. The method of claim 2 wherein obtaining the first and second chromophore concentration measurements comprises:
   measuring light remittance comprising at least four light wavelengths using the optical sensor;
   computing a scaled second derivative of the remitted light; and
   computing a chromophore concentration using the scaled second derivative.

4. The method of claim 2 wherein the coefficient yields an index that is sensitive to changes in a relative concentration of the first form of the chromophore to a total concentration of the first form and the second form of the chromophore and substantially insensitive to changes in the total concentration of the first and second forms of the chromophore.

5. The method of claim 1, wherein the first and second chormophore concentrations correspond to a total concentration of the first and the second forms of the chormophore.

6. The method of claim 5 wherein obtaining the first and second chormophore concentration measurements comprises:
   measuring light remittance comprising at least four wavelengths using the optical sensor;
   computing a second derivative of the remitted light;
   computing a scaled second derivative of the remitted light;
   determining a correction coefficient using the scaled second derivative; and
   computing the chromophore concentration using the second derivative and the correction coefficient.

7. The method of claim 5 wherein the coefficient yields an index of a change in the chromophore concentration that is sensitive to the total concentration of the first form and the second form of the chromophore and substantially insensitive to relative changes in the concentration of the first form relative to the total concentration of the chromophore.

8. The method of claim 1 further comprising obtaining a plurality of first chromophore concentration measurements and a plurality of second chromophore concentration measurements;
   solving for a plurality of coefficient values used for computing the index using a plurality of differences between the plurality of first and second chromophore concentrations; and
   establishing a look-up table of values for the coefficient corresponding to the plurality of first chromophore concentration measurements.

9. The method of claim 8 further comprising repeating a measurement of the first concentration of the chromophore and updating the coefficient by extracting a value of the coefficient from the look-up table corresponding to the repeated measurement of the first concentration.

10. The method of claim 1 further comprising establishing a threshold applied to the index for detecting a patient condition;
comparing the index to the established threshold; and
one of generating a warning and regulating a therapy in response to the index crossing the established threshold.

11. The method of claim 10 wherein the threshold is established in response to the first concentration of the chromophore.

12. An implantable medical device for monitoring a patient condition, comprising:
an optical sensor to emit light and measure remitted light; and
a processor and associated memory configured to
obtain a first concentration of a chromophore in a vicinity of a measurement volume of the optical sensor, the chromophore present in a first form and a second form,
obtain a second concentration of the chromophore in the measurement volume corresponding to at least one of a change in a total concentration of the chromophore and a change in a relative concentration of the first form of the chromophore to the total concentration of the chromophore in the vicinity of the measurement volume,
obtain a first measurement of light remittance comprising a first light wavelength and a second light wavelength, the first light remittance measurement corresponding to the first concentration,
obtain a second measurement of light remittance comprising the first light wavelength and the second light wavelength, the second light remittance measurement corresponding to the second concentration,
solve for a coefficient for computing an index of a change in the chromophore concentration using the difference between the first and second chromophore concentrations and the first and second light remittance measurements,
measure remittance at the first light wavelength and the second light wavelength, and
compute an index of the change in chromophore concentration using the measured remittance and the coefficient.

13. The device of claim 12, wherein the first and second chromophore concentration measurements correspond to a relative concentration of the first form of the chromophore to the total concentration of the chromophore.

14. The device of claim 13 wherein obtaining the first and second chromophore concentration measurements comprises:
measuring light remittance comprising at least four light wavelengths emitted by the optical sensor;
computing a scaled second derivative of the remitted light; and
computing a chromophore concentration using the scaled second derivative.

15. The device of claim 13 wherein the coefficient yields an index that is sensitive to changes in a relative concentration of the first form of the chromophore to a total concentration of the first form and the second form of the chromophore and substantially insensitive to changes in the total concentration of the first and second forms of the chromophore.

16. The device of claim 12, wherein the first and second chormophore concentrations correspond to a total concentration of the first and the second forms of the chormophore.

17. The device of claim 16 wherein obtaining the first and second chormophore concentration measurements comprises:
measuring light remittance comprising at least four wavelengths using the optical sensor;
computing a second derivative of the remitted light;
computing a scaled second derivative of the remitted light;
determining a correction coefficient using the scaled second derivative; and
computing the chromophore concentration using the second derivative and the correction coefficient.

18. The device of claim 16 wherein the coefficient yields an index that is sensitive to the total concentration of the first form and the second form of the chromophore and substantially insensitive to changes in the concentration of the first form relative to the total concentration of the chromophore.

19. The device of claim 12 wherein the processor is further configured to obtain a plurality of first chromophore concentration measurements and a plurality of second chromophore concentration measurements;
solve for a plurality of coefficient values used for computing the index using a plurality of differences between the plurality of first and second chromophore concentrations; and
establish a look-up table of values for the coefficient corresponding to the plurality of first chromophore concentration measurements.

20. The device of claim 19 wherein the processor is further configured to repeat a measurement of the first concentration of the chromophore and update the coefficient by extracting a value of the coefficient from the look-up table corresponding to the repeated measurement of the first concentration.

21. The device of claim 12 further comprising at least one of a telemetry communication module and a therapy delivery module;
the processor further configured to establish a threshold applied to the index for detecting a patient condition, compare the index to the established threshold; and one of generate a warning transmitted by the telemetry module and regulating a therapy delivered by the therapy delivery module in response to the index crossing the established threshold.

22. The device of claim 21 wherein the threshold is established in response to the first concentration of the chromophore.

23. A computer-readable medium storing instructions which cause a processor of an implantable medical device system comprising an optical sensor to:
obtain a first concentration of a chromophore in a vicinity of a measurement volume of the optical sensor, the chromophore present in a first form and a second form;
obtain a second concentration of the chromophore in the vicinity of the measurement volume corresponding to a change in at least one of a total concentration of the chromophore and a relative concentration of the first form of the chromophore to the total concentration of the chromophore in the measurement volume;
obtain a first measurement of light remittance comprising a first light wavelength and a second light wavelength, the first light remittance measurement corresponding to the first concentration;
obtain a second measurement of light remittance comprising the first light wavelength and the second light wavelength, the second light remittance measurement corresponding to the second concentration;
solve for a coefficient for computing an index of a change in the chromophore concentration using the difference between the first and second chromophore concentrations and the first and second light remittance measurements;
measure remittance at the first light wavelength and the second light wavelength; and
compute an index of the change in chromophore concentration using the measured remittance and the coefficient.

* * * * *